(12) United States Patent
Tomlinson et al.

(10) Patent No.: US 6,211,250 B1
(45) Date of Patent: Apr. 3, 2001

(54) PERCUTANEOUS DELIVERY SYSTEM (75) Inventors: Rod Tomlinson; Greg Davey, both of Rowville (AU)

(73) Assignee: Soltec Research Pty Ltd. (AU)

( * ) Notice: Subject to any disclaimer, the term of this patent is extended or adjusted under 35 U.S.C. 154(b) by 0 days.

(21) Appl. No.: 09/308,574

(22) PCT Filed: Nov. 24, 1997

(86) PCT No.: PCT/AU97/00797

§ 371 Date: May 21, 1999

§ 102(e) Date: May 21, 1999

(87) PCT Pub. No.: WO98/23291

PCT Pub. Date: Jun. 4, 1998

(30) Foreign Application Priority Data

Nov. 22, 1996 (AU) .................................................. PO 3795

(51) Int. Cl.$^7$ .................................................. A61K 47/32
(52) U.S. Cl. ........................ 514/772.4; 514/946; 424/449
(58) Field of Search .......................... 424/449; 514/772.4

(56) References Cited

U.S. PATENT DOCUMENTS

| | | | |
|---|---|---|---|
| 4,393,076 | 7/1983 | Noda et al. | 424/317 |
| 4,675,009 | * 6/1987 | Hymes et al. | 424/449 |
| 4,935,241 | 6/1990 | Saitoh et al. | 424/81 |
| 4,938,964 | * 7/1990 | Sakai et al. | 424/449 |
| 4,940,579 | 7/1990 | Randen | 424/78 |
| 4,954,332 | 9/1990 | Bissett et al. | 424/59 |
| 5,081,157 | 1/1992 | Pomerantz | 514/781 |
| 5,304,368 | 4/1994 | Shernov et al. | 424/47 |
| 5,436,241 | 7/1995 | Shin et al. | 514/226.5 |
| 5,573,759 | 11/1996 | Blank | 424/60 |
| 5,674,912 | 10/1997 | Martin | 514/724 |

FOREIGN PATENT DOCUMENTS

| | | |
|---|---|---|
| 17874/88 | 12/1988 | (AU) . |
| 27266/92 | 4/1993 | (AU) . |
| 24024/95 | 11/1995 | (AU) . |
| 54022/96 | 10/1996 | (AU) . |

OTHER PUBLICATIONS

"Dermacryl® 79 For Skin Care Formulations", *Personal Care Polymers, Specialty Products from National Starch and Chemical Company*, 1994, pp. 1–7.

* cited by examiner

Primary Examiner—Peter F. Kulkosky
(74) Attorney, Agent, or Firm—Ostrolenk, Faber, Gerb & Soffen, LLP (57) ABSTRACT

The invention relates to a substantially homogenous liquid composition capable of percutaneous delivery of one or more physiologically active agents, the composition including a rate modulating polymer, a volatile solvent and at least one physiologically active agent, said rate modulating polymer being selected to enable modulation of the rate of delivery of said physiologically active agent. Methods of percutaneous delivery of active agents and of prophylactic or therapeutic antimicrobial, antifungal or antiviral treatment using the compositions of the invention are also described.

21 Claims, 5 Drawing Sheets

FIG. 6

PERCUTANEOUS DELIVERY SYSTEM

FIELD OF THE INVENTION

The present invention is concerned with a system suitable for the percutaneous delivery, particularly transdermal delivery of active agent. The invention also relates to a method of percutaneous delivery of actives and to therapeutic or prophylactic methods of treatment of a subject by percutaneous delivery of an active agent.

BACKGROUND TO THE INVENTION

The term "active agent" as used herein is intended to denote substances that have a physiological effect, for example, a drug. The term "homogenous" as used herein is intended to mean uniform throughout. The term "film forming" as used herein is intended to mean a substance capable of forming a thin layer on the surface to which it is applied and when exposed to ambient conditions. The term "liquid" as used herein is intended to mean a substance which is flowable. The term "percutaneous" as used herein is intended to mean any route of administering an active agent onto, into or through the skin of a subject so as to achieve one or more of a topical, local or systemic physiological effect.

The use of the skin as a route for delivery of drugs is of relatively recent origin. One form of delivery system is that based on the use of an adhesive transdermal patch. These transdermal patches provide an alternative non-invasive parenteral route for the delivery of drugs which may or may not be suitable for oral administration. An example of an early form of a transdermal patch is described in U.S. Pat. No. 3,598,122 where the patch is in the form of a bandage.

Conventional routes of drug administration suffer several disadvantages when compared to the percutaneous route of drug administration. The percutaneous route of delivery may allow for the controlled release of an active agent into the systemic circulation. Many drugs are poorly absorbed by traditional routes of delivery and it has been found that the percutaneous route provides an effective method of achieving improved bioavailability for those active agents.

Examples of the uses of transdermal patches include treatment of nicotine addiction using nicotine containing patches, hormone replacement therapy, treatment of travel sickness using hyoscine, angina using glyceryltrinitrate, treatment of rheumatism using flurbiprofen or ibuprofen, and intractable pain relief using fentanyl. Other examples of transdermal patches are clonidine patches for vasoconstrictor therapy and treatment of migraine (see, for example, U.S. Pat. No. 4,201,211), oestradiol patches for treatment of osteoporosis, oestradiol/norethisterone patches, and oestrogen/progesterone patches. The world therapeutic patch market is expected to increase significantly over the next few years.

Existing transdermal patches usually comprise a layer including the active and an adhesive layer and rely on the adhesive layer for attachment of the patch to the skin of a subject. This delivery system involves incorporation of the medicament into a carrier such as a polymeric matrix and/or pressure-sensitive adhesive formulation. The adhesive must adhere to the skin and permit migration of the medicament from the carrier through the skin into the bloodstream of the subject. The medicament may be included in the polymeric matrix or the adhesive layer or both.

An example of an adhesive transdermal delivery system is described in Australian patent 670033. This patent describes a dermal composition comprising a blend of a polyacrylate and a second polymer selected from polysiloxane or a hydrocarbon polymer, wherein the polyacrylate and the second polymer are mutually insoluble or immiscible polymers and a drug wherein the composition is a pressure-sensitive adhesive.

Adhesive based transdermal systems suffer a number of disadvantages. A major disadvantage is that the adhesive is responsible for an adverse skin reaction in about 30% of individuals. Current skin patches are occlusive and prevent the skin from transpiring. Moreover the skin area to which the adhesive patch may be applied is restricted to a non-hairy area of the skin that is substantially free of wrinkles, crease and folds. Furthermore, the wearer of an adhesive patch is aware of its presence because of the its inability to stretch with the skin on body movement.

In a related art there exist topical creams for delivery of active agents for treatment of certain skin diseases. One such disclosure is that of U.S. Pat. No. 4,935,241 in the name of SHIONOGI & CO LTD. This patent describes a pharmaceutical formulation for localised treatment of tinea pedis which comprises a topical cream including an active agent and an ethyl acrylate-methyl methacrylate copolymer.

An objective of the present invention is to provide a system for the percutaneous delivery of one or more active agents which system avoids, or mitigates at least in part, one or more of the disadvantages attending prior art adhesive transdermal patches. In particular, the compositions developed should be non-occlusive, rate variable and effective in delivering an active agent to have a systemic, topical or local effect upon a subject.

SUMMARY OF THE INVENTION

Accordingly, the present invention provides, in one aspect, a substantially homogenous liquid composition capable of percutaneous delivery of one or more physiologically active agents, the composition including at least one rate modulating polymer, a volatile solvent and at least one physiologically active agent, said rate modulating polymer being selected to enable modulation of the rate of delivery of said physiologically active agent.

An advantage of the present invention is that the composition of the invention can be dispensed onto, and rubbed into the skin of a subject to form a thin film on the skin surface, this film providing for the percutaneous delivery of the one or more actives contained in the composition. The composition may be applied to the selected skin surface of skin and rubbed onto the skin until a suitable thickness of film is formed. Unlike conventional transdermal patches, the transdermal system of the present invention does not require the use of an adhesive layer. Moreover, it is robust (resistant to accidental removal), waterproof and has good substantivity on the skin. It has additionally been found that the formulations according to the invention can be varied by altering the nature of the modulating polymer to alter the rate of release of the active agent into the skin of the patient. In particular it is found that the use of the modulating polymer enables the formation of a reservoir of active agent on the skin of the patient which can be absorbed by the skin at a varying rate depending on the other components of the formulation.

Although it is preferred that the skin surface be non-hairy, the presence of hair does not create as significant a problem as is the case with adhesive patches. Similarly the presence of wrinkles, creases and folds in the skin are not an impediment to the application of the composition of the invention to a particular area of the body, although it is preferable to avoid areas that have significant creasing or folds. Moreover the film that is formed is unobtrusive to the subject in that the subject is not significantly aware of its presence on the skin.

The composition according to the invention may also preferably include a second polymer which may be of opposite water affinity to the first polymer. For example, where the first polymer is hydrophobic, the second polymer may be hydrophilic and vice versa. The percutaneous composition of the invention preferably includes at least one hydrophobic polymer and at least one hydrophilic polymer, one of which is selected to enable modulation of the rate of delivery of said physiologically active agent.

Where a hydrophobic polymer and a hydrophilic polymer are used, the composition may be such that when applied to the skin, the volatile solvent may evaporate leaving a two-phase film. The formed film may include a continuous phase and a dispersed phase. The hydrophilic polymer may form the continuous phase and the hydrophobic polymer may form the disperse phase in the formed film, or vice versa.

Alternatively, the hydrophilic polymer may be soluble in the hydrophobic polymer, or vice versa so that when the volatile solvent evaporates upon application of the composition to the patients skin, the remaining film is a single phase.

Where the composition of the invention is used to form a two phase film, the active agent may be contained in the continuous phase of the film or in the disperse phase, or in both phases. It is thought that the inclusion of the active agent in the continuous phase of a formed film has the effect of increasing the release rate of the active whereas including the active in the dispersed phase slows down its rate of release.

In another aspect of the invention, there is provided a substantially homogenous liquid composition capable of percutaneous delivery of one or more physiologically active agents, the composition including a volatile solvent, at least one physiologically active agent and at least two polymers, one of which is water soluble, and one of which is selected to enable modulation of the rate of delivery of said physiologically active agent.

The second polymer may be of opposite water affinity to the first polymer. For example, where the first polymer is hydrophobic, the second polymer may be hydrophilic and vice versa. The percutaneous composition of the invention preferably includes at least one hydrophobic polymer and at least one hydrophilic polymer, one of which is selected to enable modulation of the rate of delivery of said physiologically active agent.

In a particularly preferred aspect, the present invention provides a substantially homogenous liquid composition capable of percutaneous delivery of one or more active agents, the composition including a hydrophilic polymer and an alkyl olefinic acid amide/olefinic acid or ester copolymer, at least one active agent and a volatile solvent for said hydrophilic polymer and said copolymer and optionally for the said at least one active.

In another aspect of the invention, there is provided a substantially homogenous liquid composition capable of percutaneous delivery of one or more physiologically active agents, the composition including a volatile solvent, at least one physiologically active agent, at least one modulating polymer and a thickening agent, said at least one modulating polymer being selected to enable modulation of the rate of delivery of said physiologically active agent and said thickening agent excluding ethyl cellulose. Preferably said thickening agent is soluble in both water and alcohol. More preferably, the thickening agent is a polymer, preferably a hydrophilic polymer.

A still further aspect of the invention provides a substantially homogenous liquid composition capable of percutaneous delivery of one or more physiologically active agents, the composition including a volatile solvent, at least one physiologically active agent and at least two polymers, one of which is a modulating polymer, wherein the rate of delivery of said physiologically active agent is adjustable by varying the ratio of said modulating polymer with respect to the active agent. A preferred ratio of modulating polymer:active is 1–10,000:10,000–1. The ratio will vary according to the potency of the active agent, i.e. how much active agent on a mass basis is required to achieve the physiologically effect desired. For example, for clotrimazole, the ratio of modulating polymer : active agent will be in the order of 1–10:10–1.

A still further aspect of the invention provides a substantially homogenous liquid composition capable of percutaneous delivery of one or more physiologically active agents, the composition including a volatile solvent, at least one physiologically active agent and at least two polymers, one of which is a hydrophobic polymer and one of which is a hydrophilic polymer, wherein the rate of delivery of said physiologically active agent is adjustable by varying the ratio of said hydrophobic polymer with respect to the hydrophilic polymer. A preferred ration of hydrophobic polymer: hydrophilic polymer is 1–100:100–1. A more preferred ration of hydrophobic polymer: hydrophilic polymer is 1–10:10–1.

The volatile solvent used in the compositions of the invention may be one or more pharmaceutically or veterinarially acceptable solvents. The solvent may be present in an amount of at least 50% w/w.

The compositions of the invention may include one or more skin absorption/penetration enhancers which enhance the absorption and/or penetration of the active agent. The absorption/penetration enhancers may be present in an amount of about 0.1 to 40% w/w of the composition. The absorption/penetration enhancer may be any suitable enhancer known in the art. The enhancer may be a proton accepting solvent. The rate of penetration of the active agent may also be varied by adjusting the rate of release of the penetration enhancer from the polymer.

The composition of the invention may be in the form of a solution or a dispersion. The composition may also be in the form of a gel.

Where the composition is in the form of a dispersion, the disperse phase may be in the form of microparticles, microcapsules, microspheres, microsponges or liposomes which may contain and/or be coated with the active agent. Where the disperse phase in the form of microparticles, microcapsules, microspheres or liposomes, the continuous phase may include a hydrophobic polymer or a hydrophilic polymer.

The active agent may be dispersed or dissolved in the composition of the invention and may be present in the composition in a physiologically effective amount. The concentration of active agent used in the composition of the invention may be approximately equivalent to that normally utilised for that particular agent in conventional formulations, particularly that used in conventional transdermal patch delivery systems. The amount of drug to be incorporated in the composition varies depending on the particular drug, the desired therapeutic effect, and the time span for which the device is to provide therapy. For most drugs, the passage of the drugs through the skin will be the rate-limiting step in delivery. Thus, the amount of drug and the rate of release is typically selected so as to provide transdermal delivery characterised by a zero order time dependency for a prolonged period of time. The minimum amount of drug in the system is selected based on the amount of drug which passes through the skin in the time span for which the device is to provide therapy.

Normally, the amount of drug in the system can vary from about 0.01% w/w to about 50% w/w.

The compositions may include other components such as stabilisers, plasticisers and waterproofing agents.

In yet a further aspect the present invention provides a method for the percutaneous delivery of an active agent, the method including applying a percutaneous composition in accordance with the invention to the skin of subject. The composition according to the invention may have an anti fungal, anti bacterial or anti viral activity. The subject may be human or an animal.

In yet a further aspect, the present invention provides a method for the prophylactic or therapeutic treatment of a subject including percutaneously delivering an effective amount of an active agent by application of a composition in accordance with the present invention to the skin of the subject. The subject may be human or an animal.

PREFERRED EMBODIMENT OF THE INVENTION

Examples of suitable volatile solvents include skin safe solvents such as ethanol, isopropanol or acetone.

Preferably the enhancer is a safe, skin-tolerant ester. Particularly preferred are compounds such as octyl dimethyl para amino benzoate and octyl methoxycinnamate, isoamyl para amino benzoate, octyl salicylate, glyceryl para amino benzoate, triethanolamine salicylate and octocrylene are expected to be suitable.

The modulating polymer is preferably a substantially non-occlusive film-forming polymer, for example an hydroxyalkyl cellulose. More preferably the film forming polymer is hydroxypropyl cellulose, hydroxypropylmethylcellulose, polyvinylpyrrolidone, carbomer, PVM/MA decadiene cross polymer, hydroxypropylguar, acrylate polymer or copolymer, alkyl olefinic acid amide/olefinic acid or ester copolymer octylacrylamide, octylpropenamide acrylate copolymer, aminoalkyl methacrylate copolymer, ammonio methacrylate copolymer, PVP/VA copolymer, PVA, PVM/MA butylester copolymer, shellac or alkyl acrylate/methylmethacrylate copolymer.

The hydrophilic polymer or thickening agent may be selected from any pharmaceutically or veterinarally acceptable polymer. Examples of suitable hydrophilic polymer or thickening agent include alkylcellulose and hydroxyalkyl cellulose. Preferably the hydrophilic polymer or thickening agent is hydroxypropylmethylcellulose, more preferably hydroxypropylcellulose although other hydrophilic polymers may be used, eg. polyvinylpyrrolidone, carbomer, PVM/MA decadiene cross polymer, hydroxypropylguar etc.

The hydrophobic polymer may be acrylate polymer or copolymer. Preferably the hydrophobic polymer is a carboxylated acrylic polymer or copolymer. The hydrophobic polymer may also be an alkyl olefinic acid amide/olefinic acid or ester copolymer. The hydrophobic polymer is more preferably an octylacrylamide, octylpropenamide acrylate copolymer, aminoalkyl methacrylate copolymer, ammonio methacrylate copolymer, PVP/VA copolymer, PVA, PVM/MA butylester copolymer, shellac or alkyl acrylate/methylmethacrylate copolymer The overall polymer content of the composition of the invention may be up to 50% w/w.

The hydrophilic polymer may be present in an amount of up to about 50% w/w in the composition of the invention.

The hydrophilic polymer, or thickening agent may be preferably present in an amount of about 0.5 to 30% w/w of the composition of the invention. More preferably, the hydrophilic polymer is present in an amount of 0.05 to 10% w/w of the composition, most preferably 1.0 to 5.0% w/w of the composition.

The hydrophobic polymer may be present in an amount up to about 50% w/w. The hydrophobic polymer may be present in an amount of about 0.001 to 30% of the composition of the invention. Preferably, the hydrophobic polymer is present in an amount of 1.0 to 10% of the composition, more preferably 1.5 to 6.0%.

The active agent may be any suitable compound. The active agent may be a pharmaceutical or veterinary agent. The active agent may be a drug that is normally delivered by oral, parenteral, percutaneous or rectal route. The active agent may be a prodrug.

Examples of active drugs that can be administered by the novel transdermal drug delivery system of this invention include, but are not limited to:

Cardioactive medications, for example, organic nitrates such as nitroglycerine, isosorbide dinitrate, and isosorbide mononitrates; quinidine sulfate; procainamide; thiazides such as bendroflumethiazide, chlorothiazide, and hydrochlorothyazide; nifedipine; nicardipine; adrenergic blocking agents, such as timolol and propranolol; verapamil; diltiazem; captopril; clonidine and prazosin.

Androgenic steroids, such as testosterone, methyltestosterone and fluoxymesterone.

Estrogens, such as conjugated estrogens, esterified estrogens, estropipate, 17beta estradiol, 17beta-estradiol valerate, equilin, mestranol, estrone, estriol, 17beta-ethinyl estradiol, and diethylstilboestrol. Progestational agents, such as progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17alpha hydroxyprogesterone, dydrogesterone, dimethisterone, ethinylestrenol, norgestrel, demegestone, promegestone, and megestrol acetate.

Drugs having an action on the central nervous system, for example sedatives, hypnotics, antianxiety agents, analgesics and anaesthetics, such as chloral, buprenorphine, naloxone, haloperidol, fluphenazine, pentobarbital, phenobarbital, secobarbital, codeine, lidocaine, tetracaine, dyclonine, dibucaine, methocaine, cocaine, procaine, mepivacaine, bupivacaine, etidocaine, prilocaine, benzocaine, fentanyl, and nicotine.

Nutritional agents, such as vitamins, essential amino adds and essential fats.

Anti-inflammatory agents, such as hydrocortisone, cortisone, dexamethasone, fluocinolone, triamcinolone, medrysone, prednisolone, flurandrenolide, prednisone, halcinonide, methylprednisolone, flurandrenolide, prednisone, halcinonide, methylprednisolone, fludrocortisone, corticosterone, paramethasone, betamethasone, ibuprofen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like.

Antihistamines, such as diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, and chlorpheniramine.

Respiratory agents, such as theophilline and beta2-adrenergic agonists such as albuterol, terbutaline, metaproterenol, ritodrine, carbuterol, fenoterol, quinterenol, rimiterol, solmefamol, soterenol, and tetroquinol.

Sympathomimetics, such as dopamine, norepinephrine, phenylpropanolamine, phenylephrine, pseudoephedrine, amphetamine, propylhexedrine and epinephrine. Miotics, such as pilocarpine, and the like. 12. Cholinergic agonists, such as choline, acetylcholine, methacholine, carbachol, bethanechol, pilocarpine, muscarine, and arecoline.

Antimuscarinic or muscarinic cholinergic blocking agents such as atropine, scopolamine, homatropine, methscopolamine, homatropine methylbromide, methantheline, cyclopentolate, tropicamide, propantheline, anisotropine, dicyclomine, and eucatropine. Mydriatics, such as atropine, cyclopentolate, homatropine, scopolamine, tropicamide, eucatropine and hydroxyamphetamine.

Psychic energizers such as 3-(2-aminopropyl)indole, 3-(2-aminobutyl)indole, and the like.

Anti-infectives, such as antibiotics, including penicillin, tetracycline, chloramphenicol, sulfacetamide, sulfamethazine, sulfadiazine, sulfamerazine, sulfamethizole and sulfisoxazole; antivirals, including idoxuridine; antibacterials, such as erythromycin and clarithromycin; and other anti-infectives including nitrofurazone and the like.

Dermatological agents, such as vitamins A and E.

Humoral agents, such as the prostaglandins, natural and synthetic, for example PGE1, PGF2alpha, and PGF2alpha, and the PGE1 analog misoprostol.

Antispasmodics, such as atropine, methantheline, papaverine, cinnamedrine, and methscopolamine.

Antidepressant drugs, such as isocarboxazid, phenelzine, tranylcypromine, imipramine, amitriptyline, trimipramine, doxepin, desipramine, nortriptyline, protriptyline, amoxapine, maprotiline, and trazodone.

Anti-diabetics, such as insulin, and anticancer drugs such as tamoxifen and methotrexate.

Anorectic drugs, such as dextroamphetamine, methamphetamine, phenylpropanolamine, fenfluramine, diethylpropion, mazindol, and phentermine.

Anti-allergenics, such as antazoline, methapyrilene, chlorpheniramine, pyrilamine and pheniramine.

Tranquilizers, such as reserpine, chlorpromazine, and antianxiety benzodiazepines such as alprazolam, chlordiazepoxide, clorazepate, halazepam, oxazepam, prazepam, clonazepam, flurazepam, triazolam, 1orazepam and diazepam.

Antipsychotics, such as thiopropazate, chlorpromazine, triflupromazine, mesoridazine, piperacetazine, thioridazine, acetophenazine, fluphenazine, perphenazine, trifluoperazine, chlorprathixene, thiothixene, haloperidol, bromperidol, loxapine, and molindone.

Decongestants, such as phenylephrine, ephedrine, naphazoline, Antipyretics, such as aspirin, salicylamide, and the like.

Antimigrane agents, such as dihydroergotamine and pizotyline.

Drugs for treating nausea and vomiting, such as chlorpromazine, perphenazine, prochlorperazine, promethazine, triethylperazine, triflupromazine, and trimeprazine.

Anti-malarials, such as the 4-aminoquinolines, alpha-aminoquinolines, chloroquine, and pyrimethamine.

Anti-ulcerative agents, such as misoprostol, omeprazole, and enprostil.

Peptides and proteins, such as drugs for Parkinson's disease, spasticity, and acute muscle spasms, such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, insulin, erythropoietin and growth hormone.

Anti-estrogen or hormone agents, such as tamoxifen or human chorionic gonadotropin.

Nucleotides and nucleic acids (eg. DNA).

The active agents can be present in the composition in different forms, depending on which form yields the optimum delivery characteristics. Thus, in the case of drugs, the drug can be in its free base or acid form, or in the form of salts, esters, or any other pharmacologically acceptable derivatives, or as components of molecular complexes.

The utility of the invention is described as follows using various examples and graphs. The examples are by no means extensive and do not set boundaries for the invention in any way. The purpose of the examples is to provide evidence of the function of the invention and advantages thereof.

In the examples provided, the effectiveness of the composition according to the invention as a diffusion controlling film is shown. It can be demonstrated that the system can be used with transdermal penetration enhancers to modify the transdermal flux rate of active molecules. It can also be used with or without penetration enhancers to effectively retain active substances on the top layers of skin or to provide a sustained rate of release of active into the skin.

Some examples also highlight the ability of the system to provide wash resistance.

EXAMPLE A

A composition in accordance with the invention was prepared by combining the following components in a stirred vessel at ambient temperature:

| Component | Amount (w/w) |
|---|---|
| Ketoprofen | 2.5% |
| Klucel (hydroxypropyl cellulose) | 3.0% |
| Acrylate/octylpropenamide copolymer | 3.8% |
| Alcohol 100 | 90.7% |

The composition formed was in the form of a clear solution. When applied to the skin and spread out on the skin surface formed a substantially clear thin film.

EXAMPLE B

| Component | Amount (w/w) |
|---|---|
| Ketoprofen | 2.5% |
| Klucel (hydroxypropyl cellulose) | 2.5% |
| Acrylate/octylpropenamide copolymer | 3.0% |
| * Benzyl Benzoate | 3.0% |
| Alcohol to | 100% |

* enhancer

EXAMPLE C

| Component | Amount (w/w) |
|---|---|
| Ibuprofen | 2.5% |
| Klucel G | 3.0% |
| Ethanol | to 100% |

In Vitro Diffusion Measurements

Shed Snake Skin.

The Children's Python shed snake skin was obtained during natural shedding and the dorsal skin was used. Shed snake skin has shown to be a suitable model membrane for human skin by Itoh, et al., Use of Shed Snake Skin as a Model Membrane for In Vitro Percutaneous Penetration Studies: Comparison with Human Skin Pharm. Res., 7 (10), 1042–1047, 1990; and Rigg, et al; Shed Snake Skin and Hairless Mousse Skin as Model Membranes for Human Skin During Permeation Studies, J. Invest. Dermatol., 94; 235–240, 1990.

Method of Conducting In-Vitro Skin Diffusion Experiments in Horizontal Diffusion Cells A modified stainless steel flow-through diffusion cell assembly based on that first shown by Cooper in J. Pharm. Sci. 73, 1984, was used to perform the experiments on diffusion of the drugs from various donor compositions through snake skin.

Topical formulations are weighed out onto the skin substrate which has an area of 0.79 cm². Active substance penetrates through the skin and into the receptor solution in the bottom section of the cell. Inlet and outlet tubes connected to the receptor chamber maintain skin conditions.

The temperature of the skin was maintained at 32° C.

The receptor solution consisted of 50% propylene glycol in water, made isotonic with 0.9% sodium chloride and preserved with 0.1% sodium azide.

The concentration of applied drug in each diffusion cell sample was measured using high pressure liquid chromatography (HPLC) and absorbance detection. The results reported for each experiment are average values of the replicate diffusion cells. The assay conditions used for each different drug are given in each example.

EXAMPLE 1

The in vitro diffusion cell method described above was used to demonstrate that ibuprofen penetrates through skin using this system. The formulations tested are described in the table below.

| Material | Gel 1 % w/w | Gel 2 % w/w | Gel 3 % w/w | Control % w/w |
|---|---|---|---|---|
| Ibuprofen | 5.0 | 5.0 | 5.0 | 5.0 |
| Octyl Salicylate | 5.0 | 3.0 | 5.0 | 3.0 |
| Hydroxypropyl Cellulose | 2.2 | 2.2 | 2.2 | 2.2 |
| Dermacryl ™ 79 | 0.001 | 0.001 | 0.001 | — |
| Water | — | 20.0 | 15.0 | 23.8 |
| Ethanol | to 100.0 | to 100.0 | to 100.0 | to 100.0 |

N.B. Dermacryl ™ 79 – Acrylates/t-octylpropenamide copolymer

Samples were assayed as per the method described earlier.

The detection wavelength was 210 nm and the mobile phase consisted of 60% acetonitrile, 0.1% $H_3PO_4$, pH=3 adjusted with NaOH.

Figure 1:
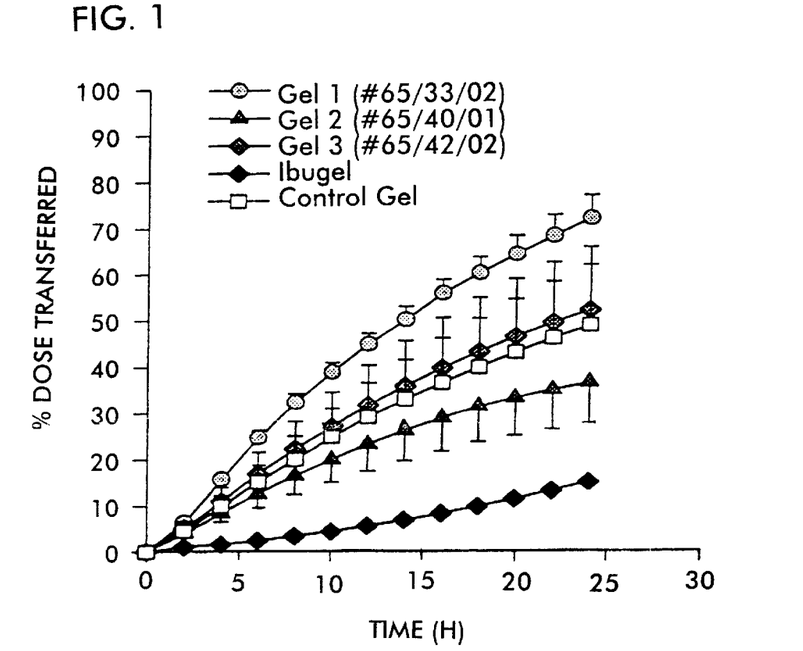
FIG. 1 is a plot of the percent of applied dose of Ibuprofen transferred across shed snake skin in vitro from different gel formulations according to the invention. The error bars represent the SEM.

FIG. 1 shows the plot of percent dose transferred versus time for the respective formulations. Error bars represent the standard error of the mean.

EXAMPLE 2

The same in-vitro diffusion cell method described was also used to demonstrate that flurbiprofen (another NSAID) penetrates skin from this system.

The following formulations were tested:

| Material | Control % w/w | F65/57/02 % w/w |
|---|---|---|
| Flurbiprofen | 5.0 | 5.0 |
| Dermacryl ™ 79 | 0.001 | 0.001 |
| Hydroxypropyl Cellulose | 2.2 | 2.2 |
| Octyl Salicylate | — | 5.0 |
| Deionised Water | 15.0 | 15.0 |
| Ethanol 95% | 77.7 | 72.7 |

Samples were assayed according to the general procedure outlined earlier.

The detection wavelength was 247 nm and the mobile phase consisted of 60% acetonitrile, 0.1% $H_3PO_4$ at pH 3 adjusted with NaOH.

Figure 2:
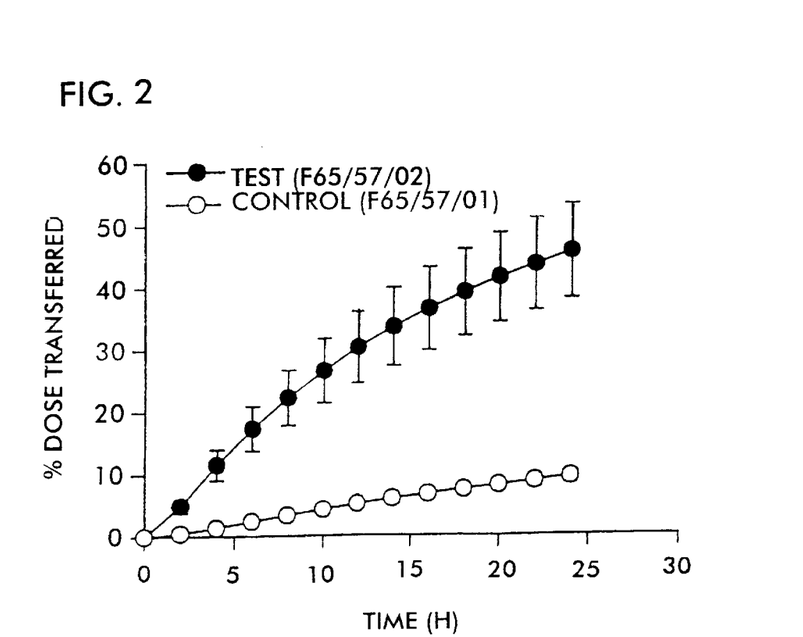
FIG. 2 is a plot of the percent of the applied dose transferred across shed snake skin in vitro from Flurbiprofen gels. The error bars represent the SEM. P=0.002 (paired t-test relative to control).

FIG. 2 shows the plot of % dose transferred versus time for the formulations. Error bars represent the standard error of the mean.

EXAMPLE 3

In vitro penetration studies were used to demonstrate that ketoprofen penetrates skin and that the rate of penetration could be modified by inclusion of higher levels of Dermacryl™ 79.

The formulations tested were as follows:

| Material | 71/05/01 % w/w | 71/05/02 % w/w | 71/05/03 % w/w | 71/05/04 % w/w | 71/05/05 % w/w |
|---|---|---|---|---|---|
| Ketoprofen | 2.5 | 5.0 | 2.5 | 2.5 | 2.5 |
| Octyl Salicylate | 2.5 | 5.0 | 2.5 | 2.5 | — |
| Dermacryl ™ 79 | 0.05 | 0.05 | 2.5 | 10.0 | 0.05 |
| Klucel ™ | 2.2 | 2.2 | 2.2 | 2.2 | 2.2 |
| Ethanol 95% | to 100.0 | to 100.0 | to 100.0 | to 100.0 | to 100.0 |

Figure 3:
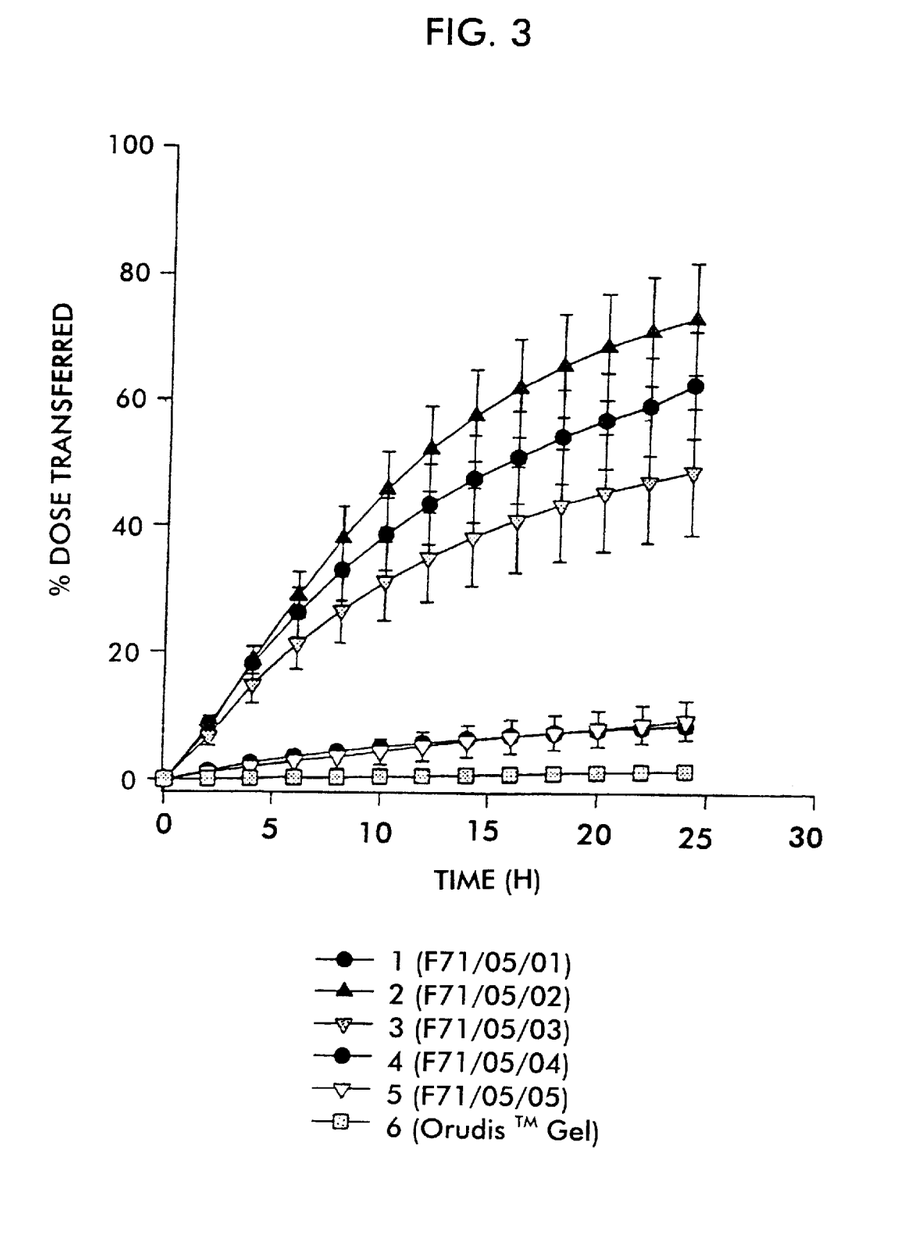
FIG. 3 is a plot of the percent of applied dose of Ketoprofen transferred across shed snake skin in vitro from different gel formulations according to the invention. The error bars represent the SEM.

FIG. 3 shows the plot of % dose transferred versus time for each formulation. This shows that by adjusting the ratio of the modulating polymer:active and/or hydrophobic polymer:hydrophilic polymer, the rate of the release of Ketoprofen into the skin of the subject can be varied. In particular, the graph demonstrates that the penetration enhancement can be controlled by varying the level of Dermacryl™ 79 in the gel.

Samples were assayed according to the general procedure outlined earlier. The detection wavelength was 255 nm and the mobile phase consisted of 55% acetonitrile, 0.1% $H_3PO_4$ at pH 3 adjusted with NaOH.

EXAMPLE 4

In order to demonstrate the ability of the composition according to the invention to produce water resistant films capable of increasing the skin substantivity of actives the following testing was conducted.

An in vivo experiment was conducted on a 1% clotrimazole gel according to the invention versus commercial clotrimazole cream (1% clotrimazole) to test for substantivity and wash resistance.

The gel formulation according to the invention was as follows:

2.5% w/w Klucel™ (Hydroxypropylcellulose)
3.2% w/w Dermacryl™ 79 (Acrylates/octylpropenamide copolymer)
1.0% w/w Clotrimazole
to 100% w/w Ethanol Each product was applied to the forearm of the subject and allowed to dry thoroughly.

At 6 and 24 hours after application the active remaining on the skin was extracted using warm ethanol.

A further condition used was a thirty second immersion in a soap solution at the 10 hour time point.

Figure 4:
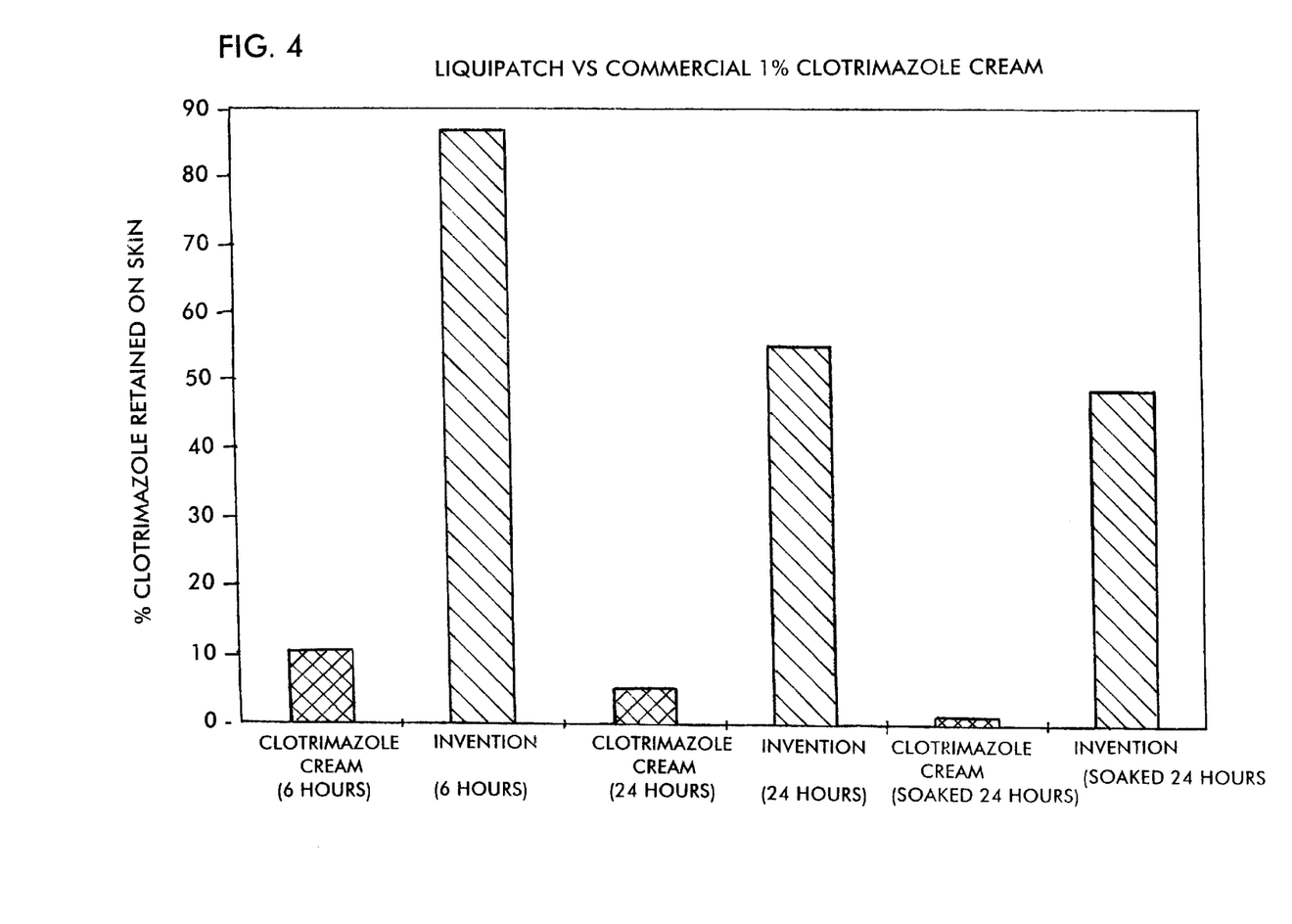
FIG. 4 is a graph of the percent of applied dose of Canesten™ and a formulation according to the invention retained on the skin after a given time and under given conditions.

The results of the trial are depicted in FIG. 4.

The results clearly demonstrate that significantly more clotrimazole remains on the skin after application of the gel compared with the commercial clotrimazole cream.

In fact greater than 50% of clotrimazole originally applied is still present after 24 hours compared with approximately 5% for the commercial clotrimazole cream.

Further, the results demonstrate the wash resistance of the gel.

The soaking of the film removed only a small portion of clotrimazole from the gel formulation whereas after soaking the commercial clotrimazole cream, only about 1% of the original dose of clotrimazole remained.

EXAMPLE 5

To demonstrate the activity of clotrimazole in the gel formulation according to the invention after application the following experiment was conducted.

A series of 1% clotrimazole gels prepared according to the invention and a commercial 1% clotrimazole cream were subjected to a zone of inhibition test against *Candida albicans*.

The gels and cream were applied to round glass cover slips of 5 $cm^2$ each. The application rate for all products was 5 $mg/cm^2$.

After drying, the coated side of the slides were placed on MEA plates which had been previously seeded with a culture of *C. albicans*. The plates were incubated at 37° C. for 72 hours. The zone of inhibition was measured around the test slides at the end of the incubation period. Furthermore the slides were removed and an assessment of the growth of the test organism was made in the contact zone with the slide. All tests were performed in duplicate.

The formulations tested were as follows:

| Material | F65/22/02 % w/w | F65/22/01 % w/w | F65/53/01 % w/w | F65/53/02 % w/w |
|---|---|---|---|---|
| Clotrimazole | — | 1.00 | 1.00 | — |
| Klucel ™ | 2.50 | 2.50 | 2.50 | 2.50 |
| Dermacryl ™ 79 | 3.20 | 3.20 | — | — |
| Propylene Glycol | — | — | 5.00 | 5.00 |
| Ethanol | to 100.0 | to 100.0 | to 100.0 | to 100.0 |

The results of the testing are shown in the following table.

| Sample Description | Inhibition in Contact Zone | Zone mm |
|---|---|---|
| A commercial 1% clotrimazole Cream B.6C04 Exp. 3/98 | Almost Complete | 1, 1 |
| Placebo Clotrimazole Gel Form No. F65/22/02 B/N E65/22/02 | No Inhibition | 0, 0 |
| Clotrimazole 1% Gel Form No. F65/22/01 B/N E65/22/01 | Almost Complete | 4, 4 |
| Clotrimazole 1% Gel Form No. 65/53/01 | Complete | 8, 9 |
| Placebo Gel F65/53/02 | Partial | 0, 0 |

The results clearly demonstrate that the clotrimazole is biologically active within the film according to the invention and in fact is more active than the commercial clotrimazole cream.

Further, the activity of clotrimazole could be increased by addition of a plasticiser ie., propylene glycol.

EXAMPLE 6

As a demonstration of the ability to use a variety of thickeners in this invention the following formulations were prepared.

| Material | F71/37/06 % w/w | F71/37/07 % w/w | F71/37/10 % w/w | F71/37/11 % w/w | F71/37/13 % w/w | F71/57/01 % w/w |
|---|---|---|---|---|---|---|
| Carbopol ™ Ultrez 10 | 0.3 | 0.5 | — | — | — | — |
| Triethanolamine | 0.3 | — | 0.4 | — | — | — |
| PVP/VA 335 (50%) | 6.0 | — | 6.0 | — | 6.0 | — |
| Deionised Water | 30.0 | 20.0 | 30.0 | — | 30.0 | 20.0 |
| Tributylamine | — | 0.7 | — | — | — | — |
| Eudragit ™ E | — | 3.0 | — | — | — | 3.0 |
| Stabileze ™ 06 | — | — | 0.7 | 2.0 | — | — |
| Eudragit ™ RL PO | — | — | — | 3.0 | — | — |
| Ethomeen ™ C25 | — | — | — | 4.0 | — | — |
| Hydroxypropyl-methylcellulose | — | — | — | — | 2.50 | — |
| Jaguar ™ HP-120 | — | — | — | — | — | 2.0 |
| Citric Acid | — | — | — | — | — | 0.055 |
| Ethanol 95% | to 100.0 | to 100.0 | to 100.0 | to 100.0 | to 100.0 | to 100.0 |

Carbopol ™ Ultrez10 = Carbomer
PVP/VA 335 = 50% solution of PVP/VA
Eudragit ™ E = Aminoalkyl methacrylate copolymer
Stabileze ™ 06 = PVM/MA decadiene cross polymer
Eudragit ™ RLPO = Ammonio Methacrylate Copolymer
Ethomeen ™ C25 = PEG 15 Cocamine
Jaguar ™ HP-120 = Hydroxypropyl guar The respective viscosities of the gels made according to the invention was measured at 25° C. with a Brookfield RVT viscometer.

They were as follows:

Viscosity (F71/37/06, spindle 3, 10 rpm)=2,500 cps.
Viscosity (F71/37/07, spindle 5, 2.5 rpm)=112,000 cps.
Viscosity (F71/37/10, spindle 4, 5 rpm)=76,000 cps.
Viscosity (F71/37/11, spindle 4, 2.5 rpm)=40,800 cps.
Viscosity (F71/37/13, spindle 6, 5 rpm)=102,000 cps.
Viscosity (F71/57/01, Spindle 4, 10 rpm)=10,000 cps.

These viscosity measurements demonstrate that various thickeners can be used to produce suitable gels with a variety of hydrophobic polymers.

EXAMPLE 7

Comparative Example

The gel described by Shionogi, U.S. Pat. 4,935,241 dated Jun. 19, 1990, and entitled Pharmaceutical Preparation for Tinea Pedis has a cosmetically unacceptable base due to:

Lack of viscosity from ethyl cellulose making it difficult to apply.

Incompatibility between HPC or HPMC and EA/MMA.

In order to overcome these shortcomings a gel was prepared using Hydroxypropylcellulose and a compatible polymer, Dermacryl™ 79.

This product had the advantage of:

Complete miscibility between the two polymers in solution (HPC and Dermacryl™ 79).

The gel could be prepared at a large range of viscosities ie, from 100 cps to 200,000 cps depending on molecular weight and percentage of HPC used.

Hence this product had the advantage of both clarity, homogeneity and ease of application.

To test the utility of the adapted gel formulation to deliver actives into skin an in-vitro skin absorption experiment was conducted comparing the absorption of clotrimazole (an antifungal) from the composition according to the invention™, Shionogi base and A commercial clotrimazole cream™ cream. All preparations contained 1% clotrimazole.

The gel formulations used are shown below.

| Material | F65/64/01 % w/w | Shionogi Base F71/17/02 % w/w |
|---|---|---|
| Clotrimazole | 1.00 | 1.00 |
| Klucel ™ | 2.50 | — |
| Dermacryl ™ 79 | 3.20 | — |
| Ethyl Cellulose | — | 1.00 |
| Eudragit ™ NE40D | — | 10.0 |
| Ethanol 95% | to 100.0 | to 100.0 |

Eudragit ™ NE 40D = 40% dispersion of ethylacrylate/methylmethacrylate

These formulations were compared for skin penetration, and epidermal and dermal retention using the following procedure.

Clotrimazole Test Method and Table of Results
Method:
Equipment & Materials:
in-vitro Franz diffusion cell with full thickness human skin (surface area 1.23 cm$^2$, receptor volume 3.5 ml)
HPLC equipment: Shimadzu automated HPLC system with UV detection
bovine serum albumin (BSA) dissolved in phosphate buffered saline (pH 7.4) as receptor phase to mimic physiological conditions.
Experimental Protocol:
finite dosing (50 mg of each formulation)
receptor phase: 4% BSA in PBS at pH 7.4
sampling time: 0, 6, 10 and 24 hours (amount in receptor phase)
epidermis separated from the dermis following 24 hour exposure to formulation
non occlusive study
each time period and formulation conducted in triplicate
Application Procedure
50 mg of each formulation was applied to the exposed skin surface at time 0 min
Procedure was the same for all products HPLC Assay Active content determined by HPLC assay using a detection wavelength of 210 mm.

The following table shows cumulated clotrimazole concentration in receptor phase (μg/cell) at 0, 6, 10 and 24 hours and in the epidermis and dermis (μg/cm2) following application of clotrimazole gels (F65/64/01 and F71/17/02) and a commercial clotrimazole cream.

| Formulation | Receptor | | | | Epidermis at 24 hrs | Dermis at 24 hrs |
|---|---|---|---|---|---|---|
| | 0 hrs | 6 hrs | 10 hrs | 24 hrs | | |
| 1. The composition according to the invention (F65/64/01) | | | | | | |
| 1A | N | N | N | N | 114.23 | 1.72 |
| 1B | N | N | N | N | 64.01 | 2.37 |
| 1C | N | N | N | N | 69.89 | 2.60 |
| Mean ± Standard Deviation | | | | | 82.71 ± 27.45 | 2.23 ± 0.46 |
| 2. Clotrimazole Gel (Shionogi base) (F71/17/02) | | | | | | |
| 2A | N | N | N | N | 19.10 | 2.49 |
| 2B | N | N | N | N | 23.29 | 2.33 |
| 2C | N | N | N | N | 28.67 | 1.99 |
| Mean ± Standard Deviation | | | | | 23.69 ± 4.79 | 2.27 ± 0.26 |
| 3. Commercial 1% clotrimazole cream | | | | | | |
| 3A | N | N | N | N | 8.66 | 0.92 |
| 3B | N | N | N | N | 18.66 | 1.39 |
| 3C | N | N | N | N | 13.88 | 0.86 |
| Mean ± Standard Deviation | | | | | 13.74 ± 5.0 | 1.06 ± 0.29 |

N = Not Detectable

Statistical Analysis

Epidermal and dermal retention of clotrimazole following applications of each of the formulations was compared by oneway ANOVA with posthoc follow-up using Tukey-HSD (sig $p<0.05$).

Epidermal retention: Formulation 1 (clotrimazole gel F65/64/01) demonstrated significantly greater epidermal retention of clotrimazole than the other formulations tested.

Dermal retention: Formulations 1 and 2 (clotrimazole gels) demonstrated significantly greater dermal retention of clotrimazole than the commercial clotrimazole cream.

The following observations were thus made:

1. None of the formulations tested had detectable skin penetration to the receptor phase up to and including at 24 hours following application.
2. The epidermal concentrations of clotrimazole in decreasing order were Formulation 1 (F65/64/01—a product according to the invention), Formulation 2 (F71/17/02—Shionogi base) and Formulation 3 (commercial 1% clotrimazole cream). The epidermal retention of formulation 1 was significantly greater than that of the other two formulations tested.
3. The dermal concentrations of formulation 1 and 2 were similar and were significantly higher than that of the commercial clotrimazole cream.

These results were surprising and clearly demonstrate the superiority of the composition according to the invention system to deliver more clotrimazole into skin over a 24 hour period. Also the composition according to the invention was far more effective than a commercial cream for delivery of clotrimazole.

This work coupled with results shown in example 4 demonstrate that the compositions according to the invention are not only more substantive to top layers of skin but also deliver more active into skin than the commercial clotrimazole cream.

EXAMPLE 8

To demonstrate the ability of a range of hydrophobic polymers to modify the penetration of actives through skin the following experimentation was conducted.

Six different hydrophobic polymers were prepared in a base composition according to the invention using ketoprofen as the active and octyl salicylate as the penetration enhancer.

These were tested for in-vitro transdermal penetration using baby snake skin as described previously.

The following formulations were prepared:

| Material | F71/24/01 % w/w | F71/24/02 % w/w | F71/24/03 % w/w | F71/24/04 % w/w |
|---|---|---|---|---|
| Ketoprofen | 2.50 | 2.50 | 2.50 | 2.50 |
| Octyl Salicylate | 2.50 | 2.50 | 2.50 | — |
| Klucel ™ | 2.20 | 2.20 | 2.20 | 2.20 |
| PVP/VA (50%) | 20.0 | — | — | — |
| Eudragit ™ E | — | 10.0 | — | — |
| Shellac | — | — | 10.0 | — |

-continued

| Material | | | | |
|---|---|---|---|---|
| Dermacryl ™ 79 | — | — | — | 10.0 |
| Ethanol 95% | to 100.0 | to 100.0 | to 100.0 | to 100.0 |

| Material | F71/24/05 % w/w | F71/24/06 % w/w | F71/24/07 % w/w | F71/24/08 % w/w |
|---|---|---|---|---|
| Ketoprofen | 2.50 | 2.50 | 2.50 | 2.50 |
| Octyl Salicylate | 2.50 | 2.50 | 2.50 | 2.50 |
| Klucel ™ M | — | 2.20 | 2.20 | 2.20 |
| Klucel ™ JFF | 12.20 | — | — | — |
| Amphomer ® | — | — | 10.00 | — |
| Gantrez ™ ES 425 (50%) | — | — | — | 20.0 |
| Ethanol 95% | to 100.0 | to 100.0 | to 100.0 | to 100.0 |

Figure 5:
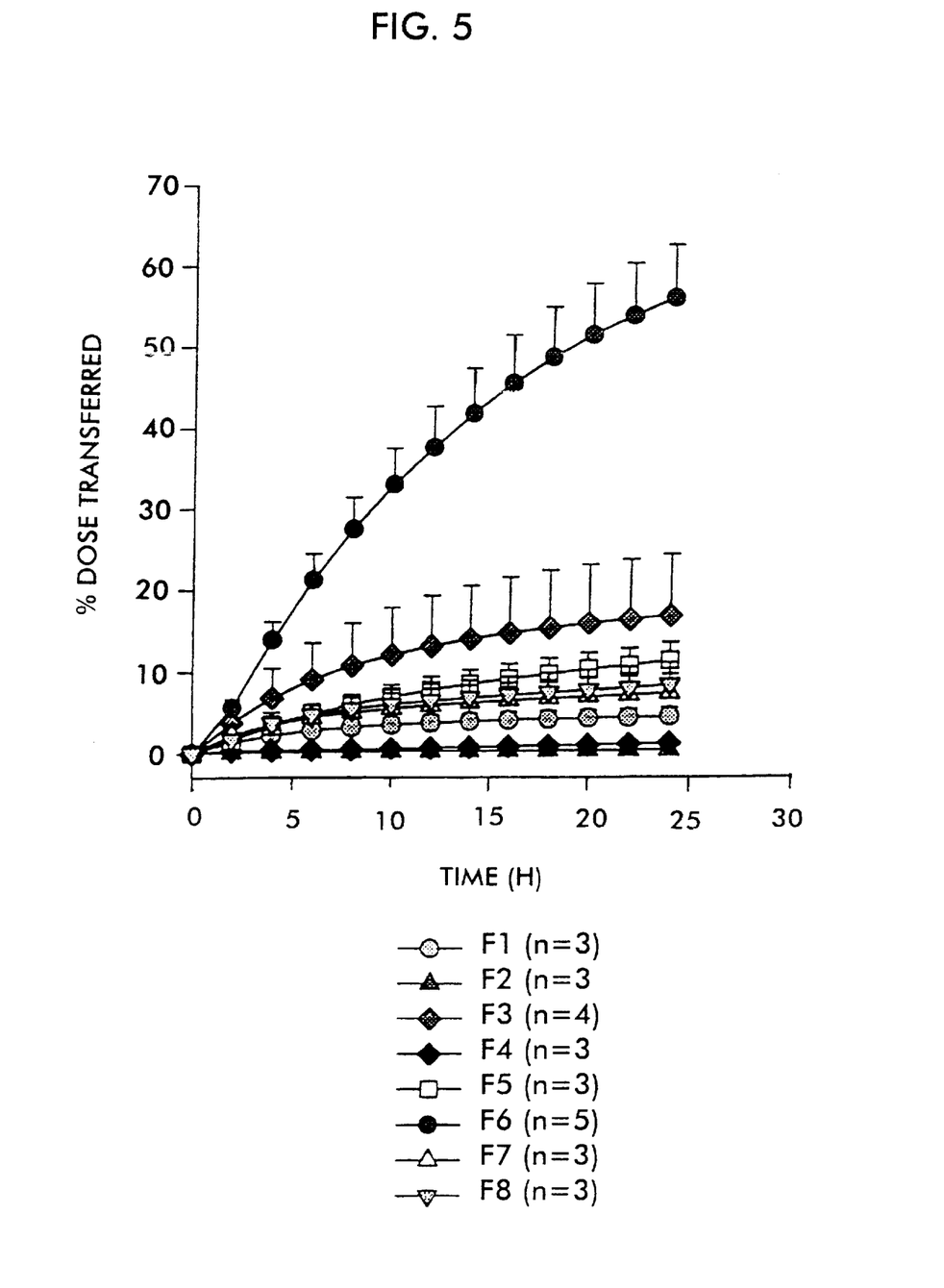
FIG. 5 is a plot of the percent of applied dose transferred across skin in vitro from Ketoprofen gels according to the invention in which the nature of the hydrophobic polymer has been altered. The error bars represent the SEM.

Klucel ™ = Hydroxypropylcellulose
Amphomer ™ = Octylacrylamide/acrylates/butylaminoethyl methacrylate copolymer
Gantrez ™ ES 425 = Butyl ester of PVM/MA copolymer The results of penetration from these gels are shown graphically in FIG. 5 wherein the % dose transferred is plotted versus time.

These results demonstrate that the penetration of ketoprofen can be controlled through the incorporation of hydrophobic polymers.

EXAMPLE 9

This example demonstrates that the composition according to the invention may also be used as a vehicle for anti-viral compounds. The active in this case was penciclovir. A gel was prepared according to the following formulation.

| | % w/w |
|---|---|
| Penciclovir | 0.30 |
| Dermacryl ™ 79 | 3.0 |
| N methyl pyrrolidone | 30.0 |
| Klucel ™ M | 2.20 |
| Deionised Water | 14.50 |
| Isopropyl alcohol | 50.0 |

This product was a clear viscous, colourless, homogenous gel suitable for application to skin to produce a localised anti-viral effect.

EXAMPLE 10

To further demonstrate the utility of the composition according to the invention for delivering NSAID's through skin, the in-vitro diffusion cell method described previously was used to assess penetration of diclofenac.

The following formulations were tested.

| Material | Control Solution % w/w | F63/55/01 % w/w |
|---|---|---|
| Dermacryl ™ 79 | — | 0.001 |
| Klucel ™ | — | 2.20 |
| Octyl Dimethyl PABA | — | 1.16 |
| Diclofenac Diethylammonium | 1.16 | 1.16 |

-continued

| Material | Control Solution % w/w | F63/55/01 % w/w |
|---|---|---|
| Water | 30.0 | — |
| Ethanol | to 100.0 | to 100.0 |

Figure 6:
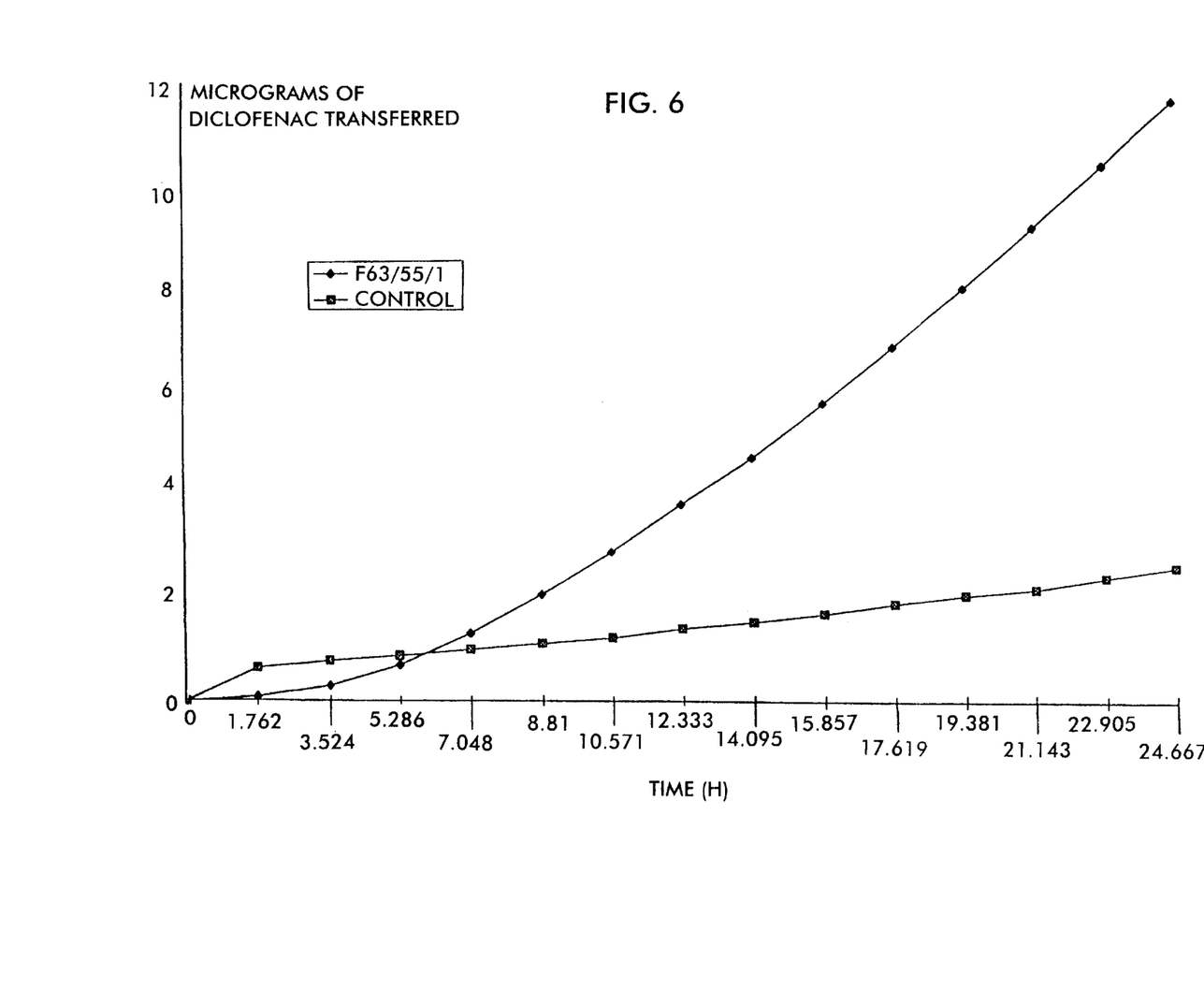
FIG. 6 is a plot of the percent of applied dose transferred across skin in vitro from Diclofenac gels according to the invention.

The skin penetration results from the formulations are shown graphically in FIG. 6.

EXAMPLE 11

Comparative Description of Shionogi patent Gels

The purpose of this example is to demonstrate that the gels of U.S. Pat. No. 4,935,241 dated Jun. 19, 1990, and entitled "Pharmaceutical Preparation for Tinea Pedis" do not meet the criteria of the compositions according to the invention, i.e homogeneity during storage.

| Material | F71/46/04 % w/w | F71/46/05 % w/w | F71/46/06 % w/w |
|---|---|---|---|
| Ethyl Cellulose | 1.00 | — | — |
| EA/MMA (40% dispersion) | 10.00 | 10.00 | 10.00 |
| Hydroxypropyl-methylcellulose | — | 1.00 | — |
| Hydroxypropylcellulose | — | — | 1.00 |
| Deionised water | 22.20 | 22.20 | 22.20 |
| Isopropyl alcohol | to 100.0 | to 100.0 | to 100.0 |

Appearance of gels after one week of storage at room temperature was as follows.

F71/46/04
Thin clear gel with a fine flocculated precipitate which had settled on bottom.

F71/46/05
Translucent, thin, lumpy gel with some solid white lumps.

F71/46/06
Clear gel which separated into two clear layers.

Although specific embodiments of the invention have been described above, it will be clear to the skilled reader that the invention is not restricted to these particular embodiments and the variations and modifications of the invention as particularly described may be made without departing from the scope of the present invention.

The claims defining the invention are as follows:

1. A substantially homogenous liquid composition capable of percutaneous delivery of one more physiologically active agents, the composition comprising at least one physiologically active agent, a volatile solvent, and a rate modulating carrier, said rate modulating carrier consisting essentially of
   (i) a hydrophilic polymer selected from the group consisting of hydroxypropylmethyl cellulose, hydroxypropyl cellulose, polyvinyl pyrrolldone, carbomer, PVM/MA decadiene cross polymer and hydroxypropylguar and copolymers thereof, said hydrophilic polymer being present in an amount of from 0.001 to 50% w/w of the total liquid composition and
   (ii) a hydrophobic polymer selected from the group consisting of octylacrylamide, octylpropenamide acrylate copolymer, aminoalkyl methacrylate copolymer, ammonio methacrylate copolymer, PVP/VA copolymer, PVA, PVM/MA butylester copolymer, shellac and alkyl acrylates and copolymers thereof, said hydrophobic polymer being present in an amount of from 0.001 to 50% w/w of the total liquid composition, the combination of hydrophilic and hydrophobic polymers being selected to enable modulation of the rate of delivery of said physiologically active ingredient.

2. A liquid composition as claimed in claim 1 wherein upon application to the skin of a subject the hydrophilic polymer forms a continuous phase, and the hydrophobic polymer is dispersed or soluble therein.

3. A liquid composition as claimed in claim 1 wherein upon application to the skin of a subject the hydrophobic polymer forms a continuous phase, and the hydrophilic polymer is dispersed or soluble therein.

4. A liquid composition as claimed in claim 2 wherein upon application to the skin of a subject said physiologically active agent is contained in said continuous phase.

5. A liquid composition as claimed in claim 2 which is in the form of a dispersion and wherein upon application to the skin of a subject said physiologically active agent is contained in said dispersed phase.

6. A liquid composition as claimed in claim 3 wherein upon application to the skin of a subject said physiologically active agent is contained in said continuous phase.

7. A liquid composition as claimed in claim 3 which is in the form of a dispersion and wherein upon application to the skin of a subject said physiologically active agent is contained in said dispersed phase.

8. A liquid composition as claimed in claim 1 wherein said hydrophilic polymer is hydroxyalkyl cellulose.

9. A liquid composition as claimed in claim 8 wherein said hydrophilic polymer is hydroxypropyl cellulose.

10. A liquid composition as claimed in claim 1 wherein said hydrophobic polymer is an octyl acrylamide or octyl-propenamide acrylate coplymer.

11. A liquid composition as claimed in claim 1 further comprising a thickening agent, said thickening agent excluding ethyl cellulose.

12. A liquid composition as claimed in claim 11 wherein said thickening agent is a polymer soluble in both alcohol and water.

13. A liquid composition according to claim 1 wherein the rate of delivery of said physiologically active agent is adjustable by varying the ratio of said rate modulating carrier to active agent.

14. A liquid composition as claimed in claim 13 further comprising a penetration enhancer, the quantity of which may be adjusted with respect to the quantity of hydrophilic and hydrophobic polymers and the active agent to alter the rate of delivery of said physiologically active agent.

15. A liquid composition according to claim 1 wherein the rate of delivery of said physiologically active agent is adjustable by varying the ratio of said hydrophilic and hydrophobic polymers with respect to each other.

16. A liquid composition according to claim 15 wherein said hydrophilic polymer is hydroxyalkyl cellulose.

17. A liquid composition according to claim 16 wherein said hydrophilic polymer is hydroxypropyl cellulose.

18. A liquid composition according to claim 15 wherein said hydrophobic polymer is an octyl acrylamide or octyl-propenamide acrylate copolymer.

19. A method of percutaneous delivery of an active agent, the method including applying a liquid composition as claimed in claim 1 to the skin of a subject.

20. A method as claimed in claim 19 wherein said subject is animal.

21. A method of prophylactic or therapeutic antimicrobial, antifungal or antiviral treatment including administering to a patient requiring such treatment an effective amount of a liquid composition as claimed in claim 1.

* * * * *

UNITED STATES PATENT AND TRADEMARK OFFICE
CERTIFICATE OF CORRECTION

PATENT NO. : 6,211,250 B1
DATED : April 3, 2001
INVENTOR(S) : Rod Tomlinson et al.

It is certified that error appears in the above-identified patent and that said Letters Patent is hereby corrected as shown below:

Column 18,
Line 51, reads "delivery of one more" should be -- delivery of one or more --.

Signed and Sealed this

Twenty-eighth Day of February, 2006

JON W. DUDAS
*Director of the United States Patent and Trademark Office*

UNITED STATES PATENT AND TRADEMARK OFFICE
CERTIFICATE OF CORRECTION

PATENT NO.         : 6,211,250 B1
APPLICATION NO. : 09/308574
DATED                  : April 3, 2001
INVENTOR(S)        : Tomlinson et al.

It is certified that error appears in the above-identified patent and that said Letters Patent is hereby corrected as shown below:

In the column 2, line 13, please amend "crease" to read --creases--.
In the column 2, line 15, please delete "the".
In the column 2, line 48, please delete "of".
In the column 2, line 49, please delete "skin".
In the column 3, line 21, line 30 and column 4, line 56, please amend "disperse" to --dispersed--.
In the column 4, line 56, after "phase", please insert --is--.
In the column 5, line 39-40, please delete "are expected to be suitable".
In the column 5, line 50, column 6, line 2 please delete the term "octylacrylamide".
In the column 6, line 34, please amend "mononitrates" to --mononitrate--.
In the column 6, line 36, please amend "rothyazide" to read --roththiazide--.
In the column 9, line 50, please amend "Mousse" to read --Mouse--.
In the column 12, lines 10 and 15, please amend "slides" to read --slips--.
In the column 12, line 17, please amend "slide" to read --slip--.
In the column 13, lines 66 and 67, please delete "<sup>TM</sup>".
In the column 15, line 3, please amend "mm" to --nm--.
In claim 1, column 18, line 64, please delete the term "octylacrylamide".
In claim 10, column 19, line 34, please delete the term "octylacrylamide".
In claim 18, column 20, line 24, please delete the term "ocylacrylamide".

Signed and Sealed this

Twenty-seventh Day of May, 2008

JON W. DUDAS
*Director of the United States Patent and Trademark Office*